(12) United States Patent
Trivedi et al.

(10) Patent No.: US 10,426,752 B2
(45) Date of Patent: *Oct. 1, 2019

(54) MENTHOL-DERIVATIVE COMPOUNDS AND USE THEREOF AS ORAL AND SYSTEMIC ACTIVE AGENTS

(75) Inventors: Harsh M. Trivedi, Somerset, NJ (US); Tao Xu, Newton, MA (US); Davide Miksa, Doylestown, PA (US); Cortney Worrell, Salem, CT (US); Chanda Macias, Somerset, NJ (US); Ying Yang, Monmouth Junction, NJ (US); Yanan Hu, San Jose, CA (US)

(73) Assignee: Colgate-Palmolive Company, New York, NY (US)

( * ) Notice: Subject to any disclaimer, the term of this patent is extended or adjusted under 35 U.S.C. 154(b) by 255 days.

This patent is subject to a terminal disclaimer.

(21) Appl. No.: 13/258,142

(22) PCT Filed: Apr. 1, 2009

(86) PCT No.: PCT/US2009/039167
§ 371 (c)(1),
(2), (4) Date: Sep. 21, 2011

(87) PCT Pub. No.: WO2010/120275
PCT Pub. Date: Oct. 21, 2010

(65) Prior Publication Data
US 2012/0014884 A1    Jan. 19, 2012

(51) Int. Cl.
| | |
|---|---|
| A61K 31/33 | (2006.01) |
| A61K 31/265 | (2006.01) |
| A61K 8/37 | (2006.01) |
| A61K 8/41 | (2006.01) |
| A61K 8/42 | (2006.01) |
| A61K 31/27 | (2006.01) |
| A61Q 11/00 | (2006.01) |

(52) U.S. Cl.
CPC ............ *A61K 31/265* (2013.01); *A61K 8/375* (2013.01); *A61K 8/411* (2013.01); *A61K 8/42* (2013.01); *A61K 31/27* (2013.01); *A61Q 11/00* (2013.01)

(58) Field of Classification Search
CPC ...... A61K 31/265; A61K 31/27; A61K 31/16; A61K 31/445; A61K 6/0067; A61K 31/33
USPC ...................... 514/512; 424/49, 55
See application file for complete search history.

(56) References Cited

U.S. PATENT DOCUMENTS

| | | | |
|---|---|---|---|
| 3,538,230 A | 11/1970 | Pader et al. | |
| 4,358,437 A | 11/1982 | Duke | |
| 5,288,480 A * | 2/1994 | Gaffar ................. | A61K 8/24 424/49 |
| 5,578,295 A | 11/1996 | Francis et al. | |
| 5,703,123 A | 12/1997 | Pelzer et al. | |
| 6,214,320 B1 | 4/2001 | Gaffar et al. | |
| 6,235,267 B1 | 5/2001 | Delli Santi et al. | |
| 6,261,540 B1 | 7/2001 | Nelson | |
| 6,372,795 B1 * | 4/2002 | Bajor et al. ................... | 514/579 |
| 7,005,225 B2 | 2/2006 | Qian et al. | |
| 7,005,255 B2 | 2/2006 | Kaddurah-Daouk et al. | |
| 7,329,489 B2 | 2/2008 | Kaddurah-Daouk et al. | |
| 7,550,258 B2 | 6/2009 | Kaddurah-Daouk et al. | |
| 7,635,556 B2 | 12/2009 | Kaddurah-Daouk et al. | |
| 2003/0069307 A1 | 4/2003 | Ley et al. | |
| 2004/0224876 A1 | 11/2004 | Jost-Price et al. | |
| 2005/0014132 A1 | 1/2005 | Kaddurah-Daouk et al. | |
| 2005/0113345 A1 | 5/2005 | Chow et al. | |
| 2005/0245494 A1 | 11/2005 | Thompson et al. | |

(Continued)

FOREIGN PATENT DOCUMENTS

| | | |
|---|---|---|
| EP | 0528468 | 2/1993 |
| EP | 1057809 | 12/2000 |

(Continued)

OTHER PUBLICATIONS

Azevedo et al. (Oral Surg Oral Med Oral Pathol Oral Radiol Endod 2009;107(1):100-104). (Year: 2009).*

(Continued)

*Primary Examiner* — Jeffrey S Lundgren
*Assistant Examiner* — Chris E Simmons

(57) ABSTRACT

The present invention discloses novel uses of specific menthol-derivative compounds of Formula 1, and compositions thereof, for methods of providing oral and systemic health care benefits, and methods of up-regulating or down-regulating periodontal disease metabolites: Formula 1 wherein, X is an oxygen atom or an NH radical; and R is an unsubstituted or substituted aryl or aliphatic radical. In some embodiments, the oral and systemic health care benefits include biofilm anti-attachment, anti-inflammation, anti-oxidant, anti-bone loss, and anti-microbial benefits. In some embodiments, the periodontal disease metabolites correspond to healthy and/or diseased oral status and allow differential diagnosis of oral health.

Formula 1

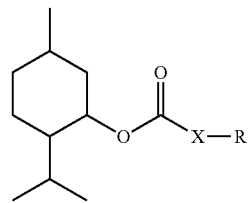

8 Claims, No Drawings

(56) References Cited

U.S. PATENT DOCUMENTS

| | | |
|---|---|---|
| 2006/0134676 A1 | 6/2006 | Kaddurah-Daouk et al. |
| 2006/0134677 A1 | 6/2006 | Kaddurab-Daouk et al. |
| 2006/0134678 A1 | 6/2006 | Kaddurab-Daouk et al. |
| 2006/0141421 A1 | 6/2006 | Braunecker et al. |
| 2007/0072203 A1 | 3/2007 | Kaddurah-Daouk et al. |
| 2007/0092476 A1 | 4/2007 | Natsch et al. |
| 2007/0160544 A1 | 7/2007 | Sreenivasan |
| 2008/0027146 A1 | 1/2008 | Fiorellini et al. |

FOREIGN PATENT DOCUMENTS

| | | |
|---|---|---|
| EP | 1210928 | 6/2002 |
| EP | 1284145 | 2/2003 |
| EP | 1466949 | 10/2004 |
| EP | 1925292 | 5/2008 |
| GB | 2401865 | 11/2004 |
| RU | 2288698 | 12/2006 |
| RU | 2324476 | 5/2008 |
| WO | WO 95/013094 | 5/1995 |
| WO | WO 97/047282 | 12/1997 |
| WO | WO 01/048481 | 7/2001 |
| WO | WO 01/055386 | 8/2001 |
| WO | WO 01/085116 | 11/2001 |
| WO | WO04-00023 | * 12/2003 |
| WO | WO2005023749 | 3/2005 |
| WO | WO 05/039504 | 5/2005 |
| WO | WO 05/057222 | 6/2005 |
| WO | WO 05/103071 | 11/2005 |
| WO | WO 06/032664 | 3/2006 |
| WO | WO 06/034495 | 3/2006 |
| WO | WO 08/093072 | 7/2008 |
| WO | WO 09/048841 | 4/2009 |
| WO | WO 09/144179 | 12/2009 |

OTHER PUBLICATIONS

Afflitto et al., 1989, "Salivary and plaque triclosan levels after brushing with a 0.3% triclosan/copolymer/NaF dentifrice," Amer. J. Dent. 2:207-210.
Akalin et al., 2007, "Lipid Peroxidation Levels and Total Oxidant Status in Serum, Saliva and Gingival Crevicular Fluid in Patients with Chronic Periodontitis," J. Clin. Periodontol. 34(7):558-265.
Armitage, 2004, "Analysis of Gingival Crevice Fluid and Risk of Progression of Periodontitis," Periodontal. 34:109-119.
Back et al., 2007, "Increased Leukotriene Concentrations in Gingival Crevicular Fluid from Subjects with Periodontal Disease and Atherosclerosis," Atherosclerosis 193(2):389-394.
Bergamini et al., 2004, "Oxygen, Reactive Oxygen Species and Tissue Damage," Curr. Pharm. Des. 10(14):1611-1626.
Berry et al., 2004, "Xanthine Oxidoreductase and Cardiovascular Disease: Molecular Mechanisms and Pathophysiological Implications," J. Physiol. 555(Pt. 3):589-606.
Bodet et al., 2005, "Modulation of cytokine production by Porphyromonas gingivalis in a macrophage and epithelial cell co-culture model," Microbes & Infect. 7(3):448-456.
Brantzaeg et al., 1992, "Compartmentalization of lipopolysaccharide production correlates with clinical presentation in meningococcal disease," J. Infect. Dis. 166(3):650-652.
Bunnell et al., 2000, "A lipid A analog, E5531, blocks the endotoxin response in human volunteers with experimental endotoxemia," Crit. Care Med. 28(8):2713-2720.
Cannon et al., 2008, "Salivary Metabonomics: A New Objective Measure in Oral Care," Poster 14, 8th European Symposium on Saliva, May 14-17, 2008, The Netherlands.
Chapple et al., 2002, "Glutathione in Gingival Crevicular Fluid and Its Relation to Local Antioxidant Capacity in Periodontal Health and Disease," Mol. Pathol. 5501:367-373.
Ciantar et al., 2002, "Development of an in vitro Microassay for Glucose Quantification in Submicrolitre Volumes of Biological Fluid," J. Periodontal Res. 37(2):79-85.

El Moudni et al., 1995, "Purification and characterisation of a metallopeptidase of Candida albicans," J. Med. Microbiol. 43(4):282-288.
Embery et al., 1994, "Gingival Crevicular Fluid: Biomarkers of Periodontal Tissue Activity," Adv. Dent. Res. 8(2):329-336.
Fokkema et al., 2003, "Monocyte-derived RANTES is intrinsically elevated in periodontal disease while MCP-1 levels are related to inflammation and are inversely correlated with IL-12 levels," Clin. & Exp. Immunol. 131(3):477-483.
Fothergill et al., 1977, "Catabolism of L-Lysine by*Pseudomonas aureuginosa*," J. Gen. Micriobiol. 99(1):139-155.
Gaspersk et al., 2010 "Anti-NGF treatment reduces bone resorption in periodontitis," J. Dental Res. 89(5):515-520.
Golub et al., 1998, "Modulation of the Host Response in the Treatment of Periodontitis," Dent. Today 17(10):102-6, 108-9.
Golub et al., 1997, "A matrix metalloproteinase inhibitor reduces bone-type collagen degradation fragments and specific collagenases in gingival crevicular fluid during adult periodontitis," Inflamm. Res. 46:310-319.
Harrison, 2004, "Physiological Roles of Xanthine Oxidoreductase," Drug Metab. Rev. 36(2):363-375.
Heasman et al., 1993, "Changes in Crevicular Fluid Levels of Interleukin-1 Beta, Leukotriene B4, Prostaglandin E2, Thromboxane B2 and Tumour Necrosis Factor Alpha in Experimental Gingivitis in Humans," J. Periodontal Res. 28(4):241-247.
Holt et al., 2001, "Dental damage, sequelae, acid prevention," Western J. of Medicine 174(4):288-290.
Ilgenli et al., 2006, "Gingival Crevicular Fluid Matrix Metalloproteinase-13 Levels and Molecular Forms in Various Types of Periodontal Diseases," Oral Dis. 12(6):573-579.
Imbert et. al., 2002, "Effect of matrix metalloprotease inhibitors on the 95 kDa metallopeptidase of Candida albicans," J. Antibicrob. Chemother. 49(6) 1007-1010.
Ingman et al., 1996, "Matrix metalloproteinases and their inhibitors in gingival crevicular fluid and saliva of periodontitis patients," J. Clin. Periodontal. 23(12):1127-1132.
Ingman et al., 1994. "Multiple Forms of Gelatinases/Type IV Collagenases in Saliva and Gingival Crevicular Fluid of Periodontitis Patients," J. Clin. Periodontol. 21(1):26-31.
International Search Report and Written Opinion in International Application No. PCT/US10/029674 dated Nov. 12, 2010.
International Search Report and Written Opinion in International Application No. PCT/US10/029670 dated Aug. 12, 2010.
International Search Report and Written Opinion in International Application No. PCT/US09/039184 dated Jun. 25, 2010.
International Search Report and Written Opinion in International Application No. PCT/US07/060222 dated Aug. 2, 2007.
Ishikura et al., 2003, "Cloning of the Tannerella Forsythensis (Bacteriodes Forsythus) siaHI Gene and Purification of the Sialidase Enzyme," J. Med. Micriobiol. 52(Pt. 12):1101-1107.
Jackson et al., 2007, "The Production of Reactive Oxygen and Nitrogen Species by Skeletal Muscle," J. Appl. Physiol. 102(4):1664-1670.
Jahngen et al., 1984, "High-Performance Liquid Chromatography Analysis of Purine Nucleosides in Human Gingival Crevicular Fluid," Arch. Oral Biol. 29(8):607-610.
Kantarci et al., 2003, "Neutrophil-Mediated Tissue Injury in Periodontal Disease Pathogenesis: Findings from Localized Aggressive Periodontitis," J. Periodontol. 74(1):66-75.
Karthikeyan et al., 2007, "Gingival Crevicular Fluid and Serum Leptin: Their Relationship to Periodontal Health and Disease," J. Clin. Periodontol. 34(6):467-472.
Kiili et al., 2002, "Collagenase-2 (MMP-8) and collagenase-3 (MMP-13) in adult periodontitis: molecular forms and levels in gingival crevicular fluid and immunolocalisation in gingival tissue," J. Clin. Periodontol. 29(3):224-232; Erratum in: J. Clin. Periodontol. 2004, 31(2):149.
Lamster et al., 2007, "Analysis of Gingival Crevicular Fluid As Applied to the Diagnosis of Oral and Systemic Diseases," Ann. NY Acad. Sci. 1098:216-229.
Lamster, 1997, "Evaluation of Components of Gingival Crevicular Fluid As Diagnostic Tests," Ann. Periodontol. 2(1):123-137.

(56) References Cited

OTHER PUBLICATIONS

Lamster et al., 1987, "The Polyamines Putrescine, Spermidine and Spermine in Human Gingival Crevicular Fluid," Arch. Oral Biol. 32(5):329-333.
Lapp et al., 2005, "Analysis of interleukin-activated human gingival fibroblasts: modulation of chemokine responses by female hormones," J. Periodontol. 76(5):803-812.
Lawton et al., 2008, "Analysis of the Adult Human Plasma Metabolome," Pharmacogenomics 9(4):383-397.
Loos et al., 2005, "Host-Derived Diagnostic Markers for Periodontitis: Do They Exist in Gingival Crevice Fluid?" Periodontol. 39:53-72.
Lorencini et al., 2009, "Changes in MMP's and inflammatory cells in experimental gingivitis," Histol. Histopathol. 24(2):157-166.
Madianos et al., 2005, "Generation of inflammatory stimuli: how bacteria set up inflammatory responses in the gingiva," J. Clin. Periodontol. 32(Supp. 6):57-71.
Mahanonda et al., 2002, "Upregulation of co-stimulatory molecule expression and dendritic cell marker (CD83) on B cells in periodontal disease," J. Periodontal Res. 37(3):177-183.
Mantyla et al., 2003, "Gingival crevicular fluid collagenase-2 (MMP-8) test stick for chair-side monitoring of periodontitis," J. Periodontol. Res. 38(4):436-439.
McAllister et al., 2008, "Spit Tests: Searching for Biomarkers in the Salivary Proteome," Poster 37, 8th European Symposium on Saliva, May 14-17, 2008, The Netherlands.
Modeer et al., 1996, "Triclosan reduces prostaglandin biosynthesis in human gingival fibroblasts challenged with interleukin-1 in vitro," J. Clin. Periodontol. 23(10):927-933.
Nixon et al., 2000, "Cytokine responses to treponema pectinovorum and treponema denticola in human gingival fibroblasts," Infect. & Immun. 68(9):5284-5292.
Ogawa et al., 2002, "Cell activation by Porphyromonas gingivalis lipid A molecule through Toll-like receptor 4- and myeloid differentiation factor 88-dependent signaling pathway," Int. Immunol. 14(11):1325-1332.
Ozmeric, 2004, "Advances in Periodontal Disease Markers," Clin. Chim. Acta 343(1-2):1-16.
Pacher et al., 2006, "Therapeutic Effects of Xanthine Oxidases Inhibitors: Renaissance Half a Century after the Discovery of Allopurinol," Pharmacol. Rev. 58(1):87-114.
Page et al., 1991, "The role of inflammatory mediators in the pathogenesis of periodontal disease," J. Periodontol. Res. 26(3 Pt. 2):230-242
Pihlstrom et al., 2005, "Periodontal Diseases," Lancet 366(9499):1809-1820.
Pozo et al., 2005, "Longitudinal analysis of metalloproteinases, tissue inhibitors of metalloproteinases and clinical parameters in gingival crevicular fluid from periodontitis-affected patients," J. Periodontol. Res. 40(3):199-207.
Pradeep et al., 2007, "Gingival Crevicular Fluid Levels of Neopterin in Healthy Subjects and in Patients with Different Periodontal Diseases," J. Periodontol. 78(10):1962-1967.
Prapulla et al., 2007, "Gingival Crevicular Fluid VEGF Levels in Periodontal Health and Disease," J. Periodontol, 78(9):1783-1787.
Preshaw et al., 2004, "Subantimicrobial dose doxycycline as adjunctive treatment for periodontitis. A review," J. Clin. Periodontol. 31(9):697-707.
Putnins et al., 2002, "Induction of keratinocyte growth factor I Expression by lipopolysaccharide is regulated by CD-14 and toll-like receptors 2 and 4," Infect. & Immun. 70(12):6541-6548.
Qin et al., 2006, "Effect of Minocycline Hydrochloride Ointment on IL-8 in Gingival Crevicular Fluid," Wuhan Dune Xuebao [Medical Journal of Wuhan University] 27(1):75-78.
Rodier et al., 1999, "A *Candida albicans* metallopeptidase degrades constitutive proteins of extracellular matrix," FEMS Microbiol. Lett. 177(2):205-210.
Rossomando et al., 1993. "A novel method for the detection of TNF-alpha in gingival crevicular fluid," J. Periodontol. 64(5 Suppl):445-449.
Ruwanpura et al., 2004, "Prostaglandin E2 regulates interleukin-1beta-induced matrix metalloproteinase-3 production in human gingival fibroblasts," J. Dental Res. 83(3):260-265.
Search Report from the European Patent Office for Corresponding European Patent Application No. EP 1015338 dated Aug. 3, 2010.
Segal et al., 2000, "Xanthine Oxidase Contributes to Host Defense against *Burkholderia cepacia* in the p47(phox-/-) Mouse Model of Chronic Granulomatous Disease," Infect. Immun. 68(4):2374-2378.
Seymour et al., 2007, "Relationship between Periodontal Infections and Systemic Disease," Clin. Microbiol. Infect. 13(Suppl. 4):3-10.
Smalley, 1994, "Pathogenic Mechanisms in Periodontal Disease," Adv. Dent. Res. 8(2):320-328.
Sorsa et al., 1990, "The role of gingival crevicular fluid and salivary interstitial collagenases in human periodontal diseases," Arch. Oral Biol. 35 Suppl:193S-196S.
Stevens et al., 2000, "Antibacteriai Properties of Xanthine Oxidase in Human Miik," Lancet 356(9332):829-830.
Sugawara, 2003, "Host Defense Mechanisms in Oral Mucosa," Tohoku University Dental Journal 22:11-18.
Sugawara et al., 2002, "Innate immune responses in oral mucosa," J. Endotoxin Res. 8(6):465-468.
Szasz et al., 2007, "A Comparison of Arteries and Veins in Oxidative Stress: Producers, Destroyers, Function, and Disease," Exp. Biol. Med. (Maywood) 232(1):27-37.
Taba el al., 2005, "Diagnostic Biomarkers for Oral and Periodontal Diseases," Dent. Clin. North Am. 49(3):551-571.
Tatakis et al., 2005, "Etiology and pathogenesis of periodontal diseases," Dent. Clin. N. Am. 49:491-516.
Teng et al., 1992, "Gingival crevicular fluid gelatinase and its relationship to periodontal disease in human subjects," J. Periodontal Res. 27(5):544-552.
Tervahartiala et al., 2000, "The in vivo Expression of the Collagenolytic Matrix Metalloproteinases (MMP-2, -8, -13, and -14) and Matrilysin (MMP-7) in Adult and Localized Juvenile Periodontitis," J. Dental Res. 79(12):1969-1977.
Toker et al., 2006, "Effect of meloxicam on gingival crevicular fluid IL-1beta and IL1 receptor antagonist levels in subjects with chronic periodontitis, and its effects on clinical parameters," Clin. Oral Investig. 10(4):305-310.
Tsai et al., 2005, "Lipid Peroxidation: A Possible Role in the Induction and Progression of Chronic Periodontitis," J. Periodontal Res. 40(5):378-384.
Tu et al., 2009, "Cyclosporine A enhances apoptosis in gingival keratinocytes of rats and in OECM1 cells via the mitochondrial pathway," J. Periodontal Res. 44(6):767-775.
Uehara et al., 2002, "Priming of human oral epithelial cells by interferon-gamma to secrete cytokines in response to lipopolysaccharides, lipoteichoic acids and peptidoglycans," J. Med. Microbiol. 51(8):626-634.
Uehara et al., 2001, "Contrasting responses of human gingival and colonic epithelial cells to lipopolysaccharides, lipoteichoic acids and peptidoglycans in the presence of soluble CD14," Med. Microbiol. Immunol. 189(4):185-192.
Valko et al., 2007, "Free Radicals and Antioxidants in Normal Physiological Functions and Human Disease," Int. J. Biochem. Cell Biol. 39(1):44-84.
Van Dyke et al., 2003, "Resolution of inflammation: A New Paradigm for the Pathogenesis of Periodontal Diseases," J. Dent. Res. 82(2):82-90.
Wang et al., 2002, "Porphyromonas gingivalis lipopolysaccharide signaling in gingival fibroblasts CD14 and Toll-like receptors," Crit. Rev. Oral Biol. Med. 13(2):132-142.
Weinberg et al., 1998, "Epithelial antimicrobial peptides: review and significance for oral applications," Crit. Rev. Oral Biol. Med. 9(4):399-414.
Xu et al., 2004, "Effectiveness of a Triclosan/Copolymer Dentifrice on Microbiological and Inflammatory Parameters," Compend. Contin. Educ. Dent., Medline Database Accession No. NLM15645886.
Yang et al., 2006, "Eukaryotic Pathways for the Induction of Peptidase by Pathogenic Oral Bacteria," D-144, http://ieg.ou.edu/ASM2006/data/papers/D_144.htm.

(56) References Cited

OTHER PUBLICATIONS

Yoshimura, 2004, "Recognition of Periodontopathic Bacteria by Innate Immune System, " J. Japanese Soc. of Periodontol. 46:94-100.
Yoshioka et al., 2003, "Effect of hydroxamic acid-based matrix metalloproteinase inhibitors on human gingival cells and Porphyromonas gingivalis," J. Periodontol. 74(8):1219-1224.
Gallegos Olea et al., 2002, "Organic Carbonate from *Caloptropis procera* Leaves," Fitoterapia 73(3):263-265.
International Search Report and Written Opinion in International Application No. PCT/US09/039140 dated Nov. 27, 2009.
Morisscau et al., 1999, "Potent Urea and Carbamate Inhibitors of Solble Epoxide Hydrolases," PNAS 96(16):8849-8854.
International Search Report and Written Opinion in International Application No. PCT/US09/039167, dated Feb. 15, 2012.
Tsuzuki et al., 2004, "Menthol-induced Ca2+ release from presynaptic Ca2+ stores potentiates sensory synaptic transmission," J. Neurosci. 24(3):762-771.
Zimmermann, 1992, "In vitro activity of taurolidine, chlorophenol-camphor-menthol and chlorhexidine against oral pathogenic microorganisms," Arzneimittelforschun 42(9):1157-1159.

\* cited by examiner

MENTHOL-DERIVATIVE COMPOUNDS AND USE THEREOF AS ORAL AND SYSTEMIC ACTIVE AGENTS

CROSS-REFERENCE TO RELATED APPLICATIONS

The present application is a national stage entry under 35 U.S.C. § 371 of International Patent Application No. PCT/US2009/039167, filed Apr. 1, 2009, the entirety of which is hereby incorporated by reference.

FIELD OF THE INVENTION

The present invention relates to methods and compositions for providing oral and/or systemic health care benefits—including biofilm anti-attachment, anti-inflammation, anti-oxidant, anti-bone loss, and anti-microbial benefits—comprising the menthol-derivative compounds of Formula 1, or mixtures thereof, and at least one excipient. The present invention further relates to methods and compositions for up-regulating and/or down-regulating periodontal disease metabolites comprising the menthol-derivative compounds of Formula 1, or mixtures thereof, and at least one excipient.

BACKGROUND OF THE INVENTION

Periodontal disease is inflammation of some or all of the tooth's support structures including gingiva, cementum, periodontal ligament, and alveolar bone. Periodontal disease metabolites in gingival crevicular fluid correspond to healthy and/or diseased oral status and allow differential diagnosis of oral health. Oral inflammation generally results from infection of bacteria in oral biofilm—a microbial soft deposit that forms on teeth and is implicated in the occurrence of gingivitis, periodontitis, caries and other forms of periodontal disease—and destroys the attachment fibers and supporting bone that hold teeth in place. Another factor in periodontal disease is microbial-induced oxidative cell damage. Oxidative free radicals are used by the body as defense systems against antigen attacks. However, oxidative free radicals may also initiate uncontrolled chain reactions that result in host tissue damage and inflammation such as that seen in oral gingivitis. Systemic oxidative cell damage, host-tissue inflammation and bone-loss occur through similar mechanisms.

Menthol-derivative compounds are physiological cooling active ingredients that are often used to bring about a sensation of coolness on the s n or mucous membranes—i.e., the mucous membranes in the oral, nasal, and/or pharyngeal cavities—by blocking calcium channels but without any physical cooling, such as occurs for example on solvent evaporation, actually occurring.

SUMMARY OF THE INVENTION

The present invention discloses novel uses of specific menthol-derivative compounds of Formula 1:

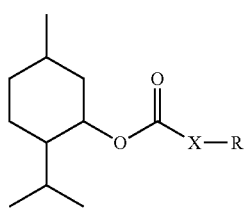

Formula 1 wherein,
X is an oxygen atom or an NH radical; and
R is an unsubstituted or substituted aryl or aliphatic radical.

It is a surprising and unexpected result of the present invention that when the proper aryl and aliphatic radicals in the proper ratio are reacted with menthol to make the compounds of the present invention, improvements in the performance of these compounds and novel uses are achieved when applied to personal care products.

In some embodiments, the present invention discloses the novel use of at least one menthol-derivative compounds of Formula 1, and compositions thereof, for methods of providing oral and systemic health care benefits. In some embodiments, the oral and systemic health care benefits include biofilm anti-attachment, anti-inflammation, anti-oxidant, anti-bone loss, and anti-microbial benefits.

In some embodiments, the present invention discloses a composition for providing oral and systemic health care benefits including at least one menthol-derivative compound of Formula 1, and at least one excipient.

In some embodiments, the present invention discloses the novel use of at least one menthol-derivative compounds of Formula 1, and compositions thereof, for methods of up-regulating or down-regulating periodontal disease metabolites, and also corresponding methods. In some embodiments, the periodontal disease metabolites correspond to healthy and/or diseased oral status and allow differential diagnosis of oral health.

In some embodiments, the present invention discloses a composition for up-regulating or down-regulating periodontal disease metabolites including at least one menthol-derivative compound of Formula 1, and at least one excipient.

BRIEF DESCRIPTION OF THE DRAWINGS

FIG. 1 shows the anti-inflammatory efficacy of a disclosed dentifrice composition.

FIG. 2 shows the anti-oxidant efficacy of a disclosed menthol-derivative compound.

FIG. 3 shows the anti-oxidant efficacy of a disclosed dentifrice composition.

FIG. 4 shows the anti-bone loss efficacy of a disclosed dentifrice composition.

FIG. 5 demonstrates the anti-microbial efficacy of a disclosed dentifrice composition.

DETAILED DESCRIPTION OF THE INVENTION

As used throughout, ranges are used as shorthand for describing each and every value that is within the range. Any value within the range can be selected as the terminus of the range. In addition, all references cited herein are hereby incorporated by reference in their entireties.

I. Methods of Use of Menthol-Derivative Compounds

In some embodiments, the present invention discloses the novel use of specific menthol-derivative compounds of Formula 1, and compositions thereof, for methods of providing oral and/or systemic health care benefits. In some embodiments, the present invention discloses a method for providing oral health care benefits. In some embodiments, the present invention discloses a method for providing systemic health care benefits. In some embodiments, the present invention discloses a method for providing at least one oral and systemic health care benefit chosen from: oral biofilm an anti-attachment, anti-inflammation, anti-oxidant, anti-bone loss, and anti-microbial benefits. In some embodiments, the present invention discloses a method for providing multiple oral and systemic health care benefits. In some embodiments, the present invention discloses a method providing multiple oral and systemic health care benefits including one or more of the following: oral biofilm anti-attachment, anti-inflammation, anti-oxidant, anti-bone loss, and anti-microbial benefits.

In some embodiments, the present invention discloses the novel use of specific menthol-derivative compounds of Formula 1, and compositions thereof, for methods of up-regulating and/or down-regulating periodontal disease metabolites. In some embodiments, the present invention discloses a method for up-regulating at least one periodontal disease metabolite. In some embodiments, the present invention discloses a method for down-regulating at least one periodontal disease metabolite. In some embodiments, the present invention discloses a method for up-regulating and/or down-regulating multiple periodontal disease metabolites.

A. Compositions of Formula 1

In some embodiments, the present invention discloses novel uses of menthol-derivative compounds of Formula 1:

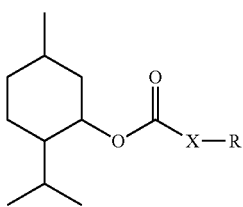

Formula 1 wherein,
X is an oxygen atom or an NH radical; and
R is an unsubstituted or substituted aryl or aliphatic radical.

In some embodiments, X is an oxygen atom. In some embodiments, X is an NH radical. In some embodiments, R is an unsubstituted aryl radical. In some embodiments, R is a substituted aryl radical. In some embodiments, R is a mono-substituted aryl radical. In some embodiments, R is a poly-substituted aryl radical. In some embodiments, R is an unsubstituted aliphatic radical. In some embodiments, R is a substituted aliphatic radical. In some embodiments, R is a mono-substituted aliphatic radical. In some embodiments, R is a poly-substituted aliphatic radical.

In some embodiments of Formula 1, R is a substituted aryl radical having up to 12 carbon atoms, wherein the substituents are chosen from: cyano radicals, hydroxyl radicals, amide radicals, ester radicals, and amine radicals.

In other embodiments of Formula 1, R is a straight, branched; or cyclic aliphatic chain radical, or R is a straight, branched, or cyclic hydroxy-aliphatic radical each having up to 10 carbon atoms.

B. Oral Biofilm Anti-Attachment Benefit

1. Description of Benefit

Oral biofilms—comprising bacteria, bacterial extracellular byproducts, proteins, lipids, and glycolipids—are matrices formed on oral surfaces that provide loci for calculus or tartar formation. In some embodiments, the present invention discloses a method for providing an oral biofilm anti-attachment benefit. In some embodiments, the method includes providing at least one menthol-derivative compound conforming to Formula 1, and compositions thereof.

In some embodiments, the oral biofilm anti-attachment benefit provided includes at least one menthol-derivative compound of Formula 1, and compositions thereof, interacting with oral bacteria to disable it from attaching to an oral surface. In some embodiments, at least one menthol-derivative compound of Formula 1, and compositions thereof, interacts with adhesins, ligands, or other moieties on the surface of oral bacteria that would ordinarily facilitate a linkage with a receptor or other moiety on the oral surface. In some embodiments, the oral biofilm anti-attachment benefit provided includes at least one menthol-derivative compound of Formula 1, and compositions thereof, interacting with an oral surface to form a protective layer, such that the bacteria and biofilm components cannot adhere to the oral or tooth surface, thereby preventing an initial anchoring layer from forming on the oral surface. In some embodiments, at least one menthol-derivative compound of Formula 1, and compositions thereof, may substantially cover an oral surface, and prevent attachment of the bacteria and other components of the biofilm matrix.

2. Specific Formula

In some embodiments, the present invention discloses a composition for providing an oral biofilm anti-attachment benefit including: at least one menthol-derivative compound conforming to Formula 1, and at least one excipient. In some embodiments, the composition for providing an oral biofilm anti-attachment benefit is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, the at least one menthol-derivative compound providing the oral biofilm anti-attachment benefit is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one menthol-derivative compound providing the oral biofilm anti-attachment benefit is:

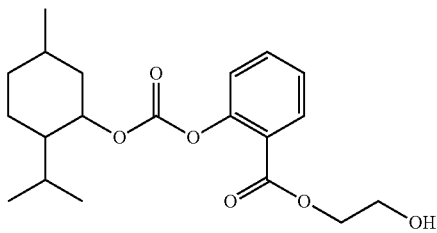

2-hydroxyethyl 2-((2-isopropyl-5-methylcyclohexyloxy)carbonyloxy)benzoate

In some embodiments, the at least one menthol-derivative compound providing the oral biofilm anti-attachment benefit is:

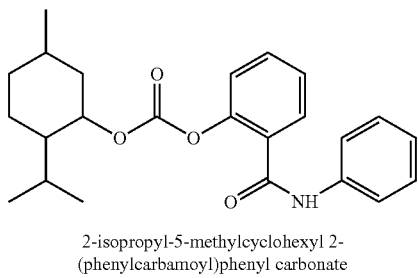 [SMILES: CC1CCC(C(C)C)C(OC(=O)Oc2ccccc2C(=O)Nc2ccccc2)C1]

2-isopropyl-5-methylcyclohexyl 2-
(phenylcarbamoyl)phenyl carbonate

In some embodiments, the at least one excipient is a member chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants preservatives, combinations thereof, and the like.

3. Test

The oral biofilm anti-attachment benefit of the menthol-derivative compounds of the present invention was investigated using the crystal violet assay (SOP No. ATO-5345-00) in a 384-well plate over a 0.0004-2500 ppm concentration range.

C. Anti-Inflammation Benefit

1. Description of Benefit

The immediate consequence of tissue damage is the release of certain chemical agents—i.e., histamine, seratonin, and the kinins—that are mediators of inflammation and evoke and intensify erythema, edema, heat, pain, and loss of tissue function.

Granulocyte macrophage colony-stimulating factor (GM-CSF) is a cytokine that functions as a white blood cell growth factor, stimulating stem cells to produce granulocytes and monocytes. Monocytes exit the circulation and migrate into tissue, whereupon they mature into macrophages. GM-CSF is thus part of the immune/inflammatory cascade, by which activation of a small number of macrophages can rapidly lead to an increase in their numbers.

Interleukin-1b (IL-1b) is a pro-inflammatory cytokine produced by macrophages, monocytes, and dendritic cells. They form an important part of the inflammatory response of the body against infection by increasing the expression of adhesion factors on endothelia cells to enable transmigration of leukocytes, the cells that fight pathogens, to sites of infection and re-set the hypothalamus thermoregulatory center, leading to an increased body temperature which expresses itself as fever and helps the body's immune system to fight infection.

Interleukin-6 (IL-6) is another interleukin that acts as a pro-inflammatory cytokine. It is secreted by T cells and macrophages to stimulate immune response to trauma, especially burns or other tissue damage leading to inflammation. IL-6 can be secreted by macrophages in response to specific microbial molecules that bind to detection molecules of the innate immune system present on the cell surface (or in intracellular compartments) which induce intracellular signaling cascades that give rise to inflammatory cytokine production.

Interleukin-8 (IL-8) is another cytokine produced by macrophages and other cell types such as epithelial cells. IL-8 is one of the major mediators of the inflammatory response and functions as a chemoattractant. It is also a potent angiogenic factor.

Tumor necrosis factor α (TNF-α) is another cytokine involved in systemic inflammation and is a member of a radical of cytokines that stimulate the acute phase reaction. The primary role of TNF-α is in the regulation of immune cells through which it is also able to induce inflammation.

In some embodiments, the present invention discloses a method for providing an anti-inflammation benefit. In some embodiments, the present invention provides an oral anti-inflammation benefit. In some embodiments, the present invention provides a systemic anti-inflammation benefit. In some embodiments, the method includes providing at least one menthol-derivative compound conforming to Formula 1, and compositions thereof.

In some embodiments, the anti-inflammation benefit provided includes at least one menthol-derivative compound of Formula 1, and compositions thereof, inhibiting the production and/or release of at least one chemical agent involved in inflammation. In some embodiments, at least one menthol-derivative compound of Formula 1, and compositions thereof, inhibits the production and/or release of GM-CSF. In some embodiments, at least one menthol-derivative compound of Formula 1, and compositions thereof, inhibits the production and/or release of IL-1b. In some embodiments, at least one menthol-derivative compound of Formula 1, and compositions thereof, inhibits the production and/or release of IL-6. In some embodiments, at least one menthol-derivative compound of Formula 1, and compositions thereof, inhibits the production and/or release of IL-8. In some embodiments, at least one menthol-derivative compound of Formula 1, and compositions thereof, inhibits the production and/or release of TNF-α. In some embodiments, at least one menthol-derivative compound of Formula 1, and compositions thereof, provides an anti-inflammation benefit efficacy comparable to existing anti-inflammatory agents. In some embodiments, at least one menthol-derivative compound of Formula 1, and compositions thereof, provides an anti-inflammation benefit efficacy comparable to triclosan.

2. Specific Formula

In some embodiments, the present invention discloses a composition for providing anti-inflammation benefit including: at least one menthol-derivative compound conforming to Formula 1, and at least one excipient. In some embodiments, the composition for providing an anti-inflammation benefit is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste. In some embodiments, a dentifrice composition comprising at least one menthol-derivative compound of FIG. 1 provides an anti-inflammation benefit efficacy comparable to existing anti-inflammatory dentifrices.

In some embodiments, the at least one menthol-derivative compound providing the anti-inflammation benefit is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one menthol-derivative compound providing the anti-inflammation benefit is:

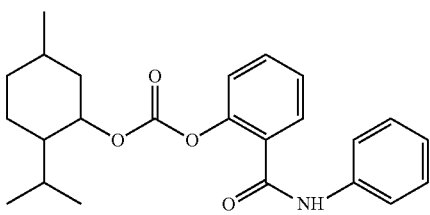

2-isopropyl-5-methylcyclohexyl 2-
(phenylcarbamoyl)phenyl carbonate

In some embodiments, the at least one menthol-derivative compound providing the anti-inflammation benefit is:

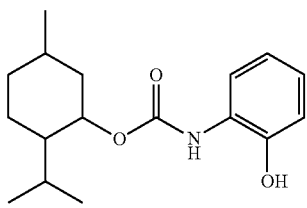

2-isopropyl-5-methylcyclohexyl 2-
hydroxyphenylcarbamate

In some embodiments, the at least one menthol-derivative compound providing the anti-inflammation benefit is:

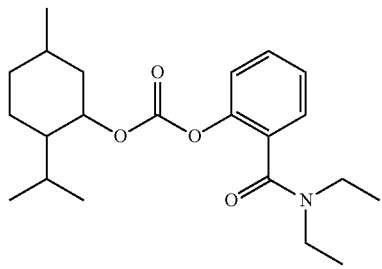

2-(diethylcarbamoyl)phenyl 2-
isopropyl-5-methylcyclohexyl carbonate

In some embodiments, the at least one excipient is a member chosen from: surfactants, desensitizing agents, whitening agents, tartar control agents, antibacterial agents, abrasives including silica, binders and thickening agents, detergents, adhesion agents foam preservatives, pH modifying agents, mouth-feel agents, sweeteners, flavorants colorants, preservatives, combinations thereof, and the like.

3. Test

The anti-inflammation test was carried out according to SOP No. ATO-5307-00 measuring the percent inhibition of $PGE_2$.

D. Anti-Oxidant Benefit

1. Description of Benefit

Oxidation is a chemical reaction that transfers electrons from a substance to an oxidizing agent and may produce free radicals that initiate tissue-damaging chain reactions and inflammation. Oxidative stress is the result of an imbalance between the production of reactive oxygen and a biological system's ability to readily detoxify the reactive intermediates or repair the resulting damage, and may be an important actor in many disease states. Antioxidants are reducing agents capable of slowing or preventing the oxidation of other molecules.

In some embodiments, the present invention discloses a method for providing an anti-oxidant benefit. In some embodiments, the method includes providing at least one menthol-derivative compound conforming to Formula 1, and compositions thereof.

In some embodiments, the anti-oxidant benefit provided includes at least one menthol-derivative compound of Formula 1, and compositions thereof, terminating a free radical chain reaction. In some embodiments, at least one menthol-derivative compound of Formula 1, and compositions thereof, removes free radical intermediates. In some embodiments, at least one menthol-derivative compound of Formula 1, and compositions thereof, inhibits other oxidation reactions by being oxidized itself without generating a free radical. In some embodiments, at least one menthol-derivative compound of Formula 1, and compositions thereof, provides an anti-oxidant benefit efficacy comparable to existing anti-oxidants. In some embodiments, at least one menthol-derivative compound of Formula 1, and compositions thereof, provides an anti-oxidant benefit efficacy comparable to Vitamin E.

2. Specific Formula

In some embodiments, the present invention discloses a composition for providing an anti-oxidant benefit including: at least one menthol-derivative compound conforming to Formula 1, and at least one excipient. In some embodiments, the composition for providing an anti-oxidant benefit is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste. In some embodiments, a dentifrice composition comprising a menthol-derivative compound of Formula 1, or mixtures thereof, provides an anti-oxidant benefit efficacy comparable to existing anti-oxidizing dentifrices.

In some embodiments, the at least one menthol-derivative compound providing the anti-oxidant benefit is, present in a composition in an amount of from 0.05 wt. % to 5 wt. %. In some embodiments, the at least one menthol-derivative compound is present in an amount of 0.1 wt % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one menthol-derivative compound providing the anti-oxidant benefit is:

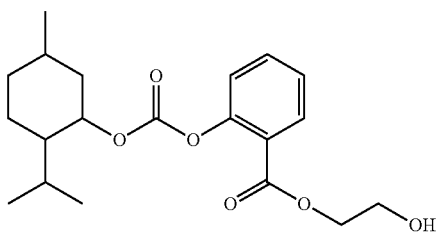

2-hydroxyethyl 2-((2-isopropyl-5-
methylcyclohexyloxy)carbonyloxy)benzoate

In some embodiments, the at least one menthol-derivative compound providing the anti-oxidant benefit is:

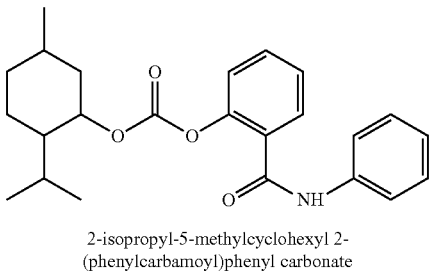 [SMILES: CC1CCC(C(C)C)C(OC(=O)Oc2ccccc2C(=O)Nc2ccccc2)C1]

2-isopropyl-5-methylcyclohexyl 2-(phenylcarbamoyl)phenyl carbonate

In some embodiments, the at least one menthol-derivative compound providing the anti-oxidant benefit is:

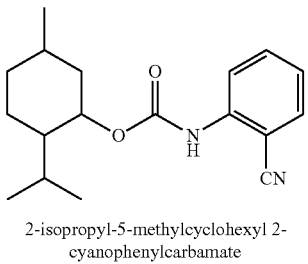 [SMILES: CC1CCC(C(C)C)C(OC(=O)Nc2ccccc2C#N)C1]

2-isopropyl-5-methylcyclohexyl 2-cyanophenylcarbamate

In some embodiments, the at least one menthol-derivative compound providing the anti-oxidant benefit is:

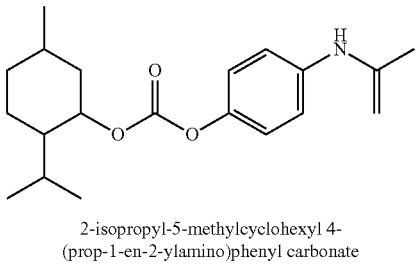 [SMILES: C=C(C)Nc1ccc(OC(=O)OC2CC(C)CCC2C(C)C)cc1]

2-isopropyl-5-methylcyclohexyl 4-(prop-1-en-2-ylamino)phenyl carbonate

In some embodiments, the at least one excipient is a member chosen from: surfactants, desensitizing agents, whitening agents, tartar control agents, antibacterial agents, abrasives including silica, binders and thickening agents detergents, adhesion agents, foam modulators, pH modifying agents, mouth-feel agents, sweeteners, flavorants, colorants, preservatives, combinations thereof, and the like.

3. Test

The anti-oxidant activity was determined using the lipid peroxidases assay (Kamiaya Biomedical Co., Seattle, Wash.) which is a colorimetric method that measures reduction of cumene hydroperoxide radicals.

E. Anti-Bone Loss Benefit

1. Description of Benefit

One of the major factors involved in bone remodeling during growth, development, and healing is matrix metalloproteases (MMPs), including interstitial collagenases such as MMP-13, that degrade the native interstitial collagens in several tissues. However, elevated levels of MMPs are observed in arthritic tissues, and MMP-13 degradation of type II collagen in cartilage is a cytokine-mediated committed step in the progression of rheumatoid arthritis and osteoarthritis. Expression of MMP-13 mRNA is stimulated by parathyroid hormone (PTH), which is substantially increased in response to cell-signaling intermediates and transcription factors including IL-1 and TNF-α.

In some embodiments, the present invention discloses a method for providing an anti-bone loss benefit. In some embodiments, the anti-bone loss benefit provided includes at least one menthol-derivative compound of Formula 1, and compositions thereof, suppressing expression of MMP-13 mRNA. In some embodiments, at least one menthol-derivative compound of Formula 1, and compositions thereof, inhibits the production and/or release of parathyroid hormone. In some embodiments, at least one menthol-derivative compound of Formula 1, and compositions thereof, inhibits the production and/or release of IL-1. In some embodiments, at least one menthol-derivative compound of Formula 1, and compositions thereof, inhibits is the production and/or release of TNF-α.

2. Specific Formula

In some embodiments, the present invention discloses a composition for providing an anti-bone loss benefit including: at least one menthol-derivative compound conforming to Formula 1, and at least one excipient. In some embodiments, the composition for providing an anti-bone loss benefit is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, the at least one menthol-derivative compound providing the anti-bone loss benefit is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound present in an amount of 0.5 wt. %.

In some embodiments, the at least one menthol-derivative compound providing the anti-bone loss benefit is:

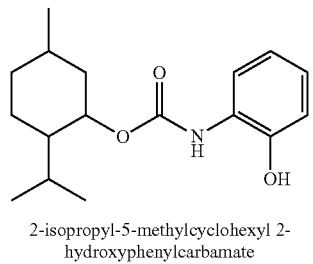 [SMILES: CC1CCC(C(C)C)C(OC(=O)Nc2ccccc2O)C1]

2-isopropyl-5-methylcyclohexyl 2-hydroxyphenylcarbamate

In some embodiments, the at least one excipient is a member chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

3. Test

The anti-MMP-13 activity was determined by measuring the inhibition of MMP-13 mRNA expression that is stimulated by parathyroid hormone (PTH).

F. Anti-Microbial Benefit

1. Description of Benefit

In some embodiments, the present invention discloses a method for providing an anti-microbial benefit. In some embodiments, the anti-microbial benefit provided includes at least one menthol-derivative compound of Formula 1, and compositions thereof, perturbing the lipid fraction of microorganism plasma membrane. In some embodiments, at least one menthol-derivative compound of Formula 1, and compositions thereof, alters microbial membrane permeability resulting leakage of intracellular materials and cell death. In some embodiments, at least one menthol-derivative compound of Formula 1, and compositions thereof, crosses microbial cell membranes, penetrating into the interior of the cell and interacting with intracellular sites critical for antimicrobial activity.

2. Specific Formula

In some embodiments, the present invention discloses a composition for providing an anti-microbial benefit including: at least one menthol-derivative compound conforming to Formula 1, and at least one excipient. In some embodiments, the composition for providing an anti-microbial benefit is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, the at least one menthol-derivative compound providing the anti-microbial benefit is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one menthol-derivative compound providing the anti-microbial benefit is:

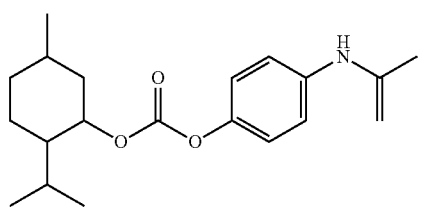

2-isopropyl-5-methylcyclohexyl 4-(prop-1-en-2-ylamino)phenyl carbonate

In some embodiments, the at least one menthol-derivative compound providing the anti-microbial benefit is:

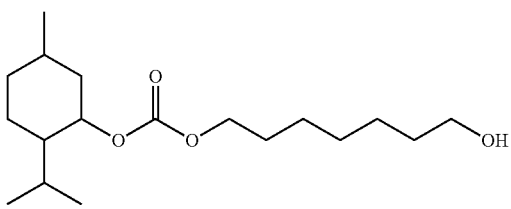

7-hydroxyheptyl 2-isopropyl-5-methycyclohexyl carbonate

In some embodiments, the at least one menthol-derivative compound providing the anti-microbial benefit is:

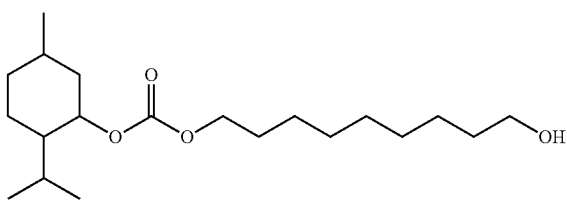

9-hydroxynonyl 2-isopropyl-5-methycyclohexyl carbonate

In some embodiments, the at least one menthol-derivative compound providing the anti-microbial benefit is:

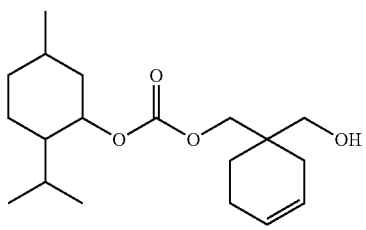

(1-(hydroxymethyl)cyclohex-3-enyl)methyl 2-isopropyl-5-methylcyclohexyl carbonate In some embodiments, the at least one menthol-derivative compound providing the anti-microbial benefit is:

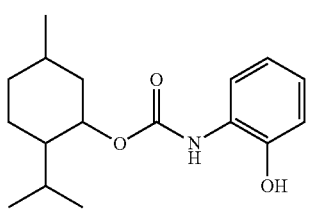

2-isopropyl-5-methylcyclohexyl 2-hydroxyphenylcarbamate

In some embodiments, the at least one menthol-derivative compound providing the anti-microbial benefit is:

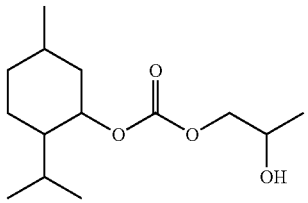

2-hydroxypropyl 2-isopropyl-5-methylcyclohexyl carbonate

In some embodiments, the at least one excipient is a member chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

3. Test

The anti-microbial test was measured according to the SOP No. ATO-5308-00 for determination of Minimal Inhibitory Concenctration (MIC).

G. Regulation of Periodontal Disease Metabolites

1. Definitions

As used herein, "healthy oral status" means the absence of gingivitis and/or periodontal disease.

As used herein, "periodontal disease" means an inflammation of the periodontium including the gingival, or gum tissue; the cementum, or outer layer of the roots of teeth; the alveolar bone, or the bony sockets into which the teeth are anchored; and the periodontal ligaments which are the connective tissue fibers that run between the cementum and the alveolar bone and includes gingivitis.

2. General Metabolites

Periodontal disease metabolites in gingival crevicular fluid correspond to healthy and/or periodontal disease oral status and allow differential diagnosis of oral health. Periodontal disease metabolites may be chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

The periodontal disease metabolites described herein were discovered using metabolomic profiling techniques. Such metabolomic profiling techniques are described in U.S. Pat. Nos. 7,005,225 and 7,329,489; and U.S. patent application Ser. Nos. 11/357,732; 11/301,077 (Publication No. 2006/0134676); Ser. No. 11/301,078 (Publication No. 2006/0134677); Ser. No. 11/301,079 (Publication No. 2006/0134678) and Ser. No. 11/405,033 (Publication No. 2007/0072203); the entire contents of which are hereby incorporated by reference.

In some embodiments, the present invention discloses the novel use of specific menthol-derivative compounds of Formula 1, and compositions thereof, for methods of up-regulating or down regulating periodontal disease metabolites. In some embodiments, the up-regulated or down-regulated metabolite is at least one compound chosen from: a compound generated by amino acid metabolism, a compound generated in urea cycle; a compound generated in glutathion conversion; a compound generated in lipid metabolism; a compound generated in carbohydrate metabolism; a compound generated by nucleic acid metabolism; vitamins; and co-factors.

3. Up-Regulation

In some embodiments, the present invention discloses a method for up-regulating periodontal disease metabolites. In some embodiments, the method for up-regulating periodontal disease metabolites includes a menthol-derivative compound of Formula 1, and compositions thereof, up-regulating at least one metabolite selected from the radical consisting of: uric acid, reduced glutathione, oxidized glutathion, ascorbic acid, and glutamine.

In some embodiments, the present invention discloses a composition for up-regulating periodontal disease metabolites including: at least one menthol-derivative compound conforming to Formula 1, and at least one excipient. In some embodiments, the composition for up-regulating periodontal disease metabolites is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, the at least one menthol-derivative compound up-regulating the periodontal disease metabolites is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one excipient is a member chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

4. Down-Regulation

In some embodiments, the present invention discloses a method for down-regulating periodontal disease metabolites. In some embodiments, the method for down-regulating periodontal disease metabolites includes a menthol-derivative compound of Formula 1, and compositions thereof, down-regulating at least one metabolite selected from the radical consisting of: inosine, hypoxanthine, guanosine, guanine, leucine isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

In some embodiments, the present invention discloses a composition for down-regulating periodontal disease metabolites including: at least one menthol-derivative compound conforming to Formula 1, and at least one excipient. In some embodiments, the composition for down-regulating periodontal disease metabolites is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, the at least one menthol-derivative compound down-regulating the periodontal disease metabolites is present in a composition in an amount of from 0.05 wt. % to 5 wt. %. In some embodiments, the at least one menthol-derivative compound is present in an amount of 0.1 wt. % to 1 wt. %. In some embodiments, the at least one menthol-derivative compound is present in an amount of 0.25 wt. % to 0.5 wt. %. In some embodiments, the at least one menthol-derivative compound is present in an amount of 0.25 wt. %. In some embodiments, the at least one menthol-derivative compound is present in an amount of 0.5 wt. %.

In some embodiments, the at least one excipient is a member chosen from: surfactants, desensitizing agents, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like.

II. Compositions Including Menthol-Derivative Compounds

A. General Compositions

In some embodiments, a composition in accordance with the present invention provides oral and/or systemic health care benefits. In some embodiments, the present invention discloses a composition for providing oral health care benefits. In some embodiments, the present invention discloses a composition for providing systemic health care benefits. In some embodiments, the present invention discloses a composition for providing at least one oral and systemic health care benefit selected from: oral biofilm anti-attachment, anti-inflammation, anti-oxidant, anti-bone loss, and anti-microbial benefits. In some embodiments, the present invention discloses a composition for providing multiple oral and systemic health care benefits. In some embodiments, the present invention discloses a composition for providing oral and systemic health care benefits including oral biofilm anti-attachment, anti-inflammation, anti-oxidant, anti-bone loss, and anti-microbial benefits.

In some embodiments, a composition in accordance with the present invention up-regulates and/or down-regulates at least one periodontal disease metabolite. In some embodiments, the present invention discloses a composition for up-regulating at least one periodontal disease metabolite. In some embodiments, the present invention discloses a composition for down-regulating at least one periodontal disease metabolite. In some embodiments, the present invention discloses a composition for up-regulating an or down-regulating multiple periodontal disease metabolites.

In some embodiments, a composition in accordance with the present invention is an oral composition suitable for use in an oral cavity. In some embodiments, the oral composition is suitable for ingestion through an oral cavity. In some embodiments, an oral composition in accordance with the present invention includes, but is not limited to: cremes, gels, pastes, foams, emulsions, suspensions, aerosols, sprays, mouthwashes, pharmaceuticals, capsules, granules lozenges, tablets, sweets and chewing gum. In some embodiments, the composition an oral care composition. In some embodiments, the oral care composition is a dentifrice composition. In some embodiments, the dentifrice composition is a member chosen from: toothpastes, gels, mouth washes, dental floss, powders, gum adhering strips, toothbrushes, and the like. In some embodiments, the dentifrice composition in accordance with the present invention is a toothpaste.

In some embodiments, a composition in accordance with the present invention is a topical composition suitable for use outside a body cavity. In some embodiments, a topical composition in accordance with the present invention includes, but is not limited to: soaps, synthetic detergents, liquid shower/bath preparations, emulsions, ointments, pastes, gels, body oils, toners, balsams, serums, powders, eau de toilettes, colognes, perfumes, waxes, aerosols, foot care products, insect-repellent products, sunscreen products, aftersun preparations, shaving or aftershave preparations, depilatory products, hair care products, nail care products, deodorants and/or antiperspirants, and cosmetic products. In some embodiments, the composition is a topical care composition. In some embodiments, the topical care composition is a member chosen from: ointments, creams, suspensions, lotions, powders, solutions, pastes, gels, sprays, aerosols, oils, and the like.

1. Oral Care Compositions

In some embodiments, an oral care composition in accordance with the present invention comprises at least one menthol-derivative compound of Formula 1, and at least one excipient. Menthol-derivative compounds suitable for use in the present invention conform to Formula 1:

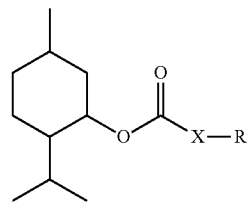

Formula 1 wherein,
X is an oxygen atom or an NH radical; and
R is an unsubstituted or substituted aryl or aliphatic radical.

In some embodiments, an oral care composition in accordance with the present invention includes at least one menthol-derivative compound of Formula 1 wherein X is an oxygen atom. In some embodiments, X is an NH radical. In some embodiments, an oral care composition in accordance with the present invention includes at least one menthol-derivative compound of Formula 1 wherein R is an unsubstituted aryl radical. In some embodiments R is a substituted aryl radical. In some embodiments, R is a mono-substituted aryl radical. In some embodiments, R is a poly-substituted aryl radical. In some embodiments, R is an unsubstituted aliphatic radical. In some embodiments, R is a substituted aliphatic radical. In some embodiments, R is a mono-substituted aliphatic radical. In some embodiments, R is a poly-substituted aliphatic radical.

In some embodiments, an oral care composition in accordance with the present invention includes at least one menthol-derivative compound of Formula 1 wherein R is a substituted aryl radical having up to 12 carbon atoms, wherein the substituents are chosen from: cyano radicals, hydroxyl radicals, amide radicals, ester radicals, and amine radicals.

In some embodiments, an oral care composition in accordance with the present invention includes at least one menthol-derivative compound of Formula 1 wherein R is a straight, branched, or cyclic aliphatic chain radical, or R is a straight, branched, or cyclic hydroxy-aliphatic radical, each having up to 10 carbon atoms.

In some embodiments, an oral care composition in accordance with the present invention includes the at least one menthol-derivative compound of Formula 1 in an effective amount of from 0.05 wt. % to 5 wt. %. In some embodiments, the at least one menthol-derivative compound is present in an effective amount of 0.1 wt. % to 1 wt. %. In some embodiments, the at least one menthol-derivative compound is present in an effective amount of 0.25 wt. % to 0.5 wt. %. In some embodiments, the at least one menthol-derivative compound is present in an effective amount of 0.25 wt. %. In some embodiments, the at least one menthol-derivative compound is present in an effective amount of 0.5 wt. %.

B. Specific Menthol-Derivative Compounds

Menthol-derivative compounds suitable for use in the present invention conform to Formula 1:

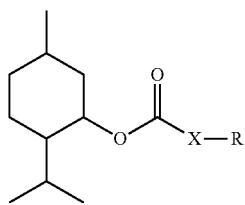

Formula 1 wherein,
X is an oxygen atom or an NH radical; and
R is an unsubstituted or substituted aryl or aliphatic radical.

In some embodiments, X is an oxygen atom. In some embodiments, X is an NH radical. In some embodiments, R is an unsubstituted aryl radical. In some embodiments, R is a substituted aryl radical. In some embodiments, R is a mono-substituted aryl radical. In some embodiments, R is a poly-substituted aryl radical. In some embodiments, R is an unsubstituted aliphatic radical. In some embodiments, R is a substituted aliphatic radical. In some embodiments, R is a mono-substituted aliphatic radical. In some embodiments, R is a poly-substituted aliphatic radical.

In some embodiments of Formula 1, R is a substituted aryl radical having up to 12 carbon atoms, wherein the substituents are chosen from: cyano radicals, hydroxyl radicals, amide radicals, ester radicals, and amine radicals.

In other embodiments of Formula 1, R is a straight, branched, or cyclic aliphatic chain radical, or R is a straight, branched, or cyclic hydroxy-aliphatic radical, each having up to 10 carbon atoms.

In some embodiments, R is:

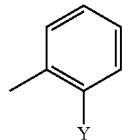

wherein Y is a hydroxyl or cyano radical.

In some embodiments, R is at least one member chosen from:

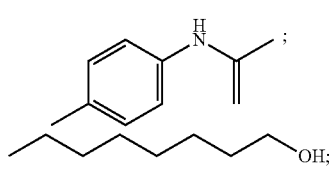

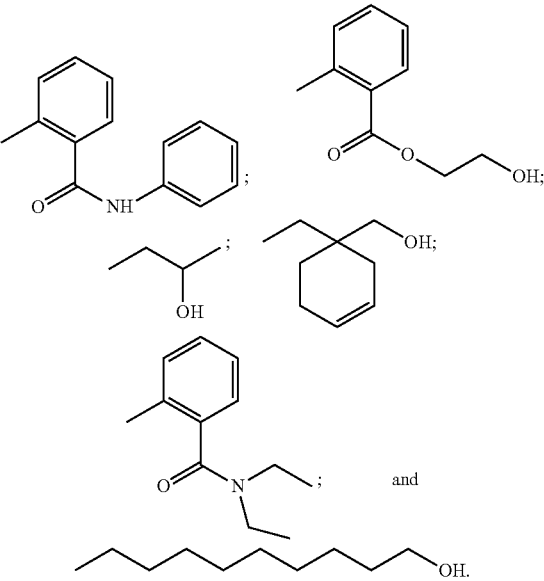

In some embodiments, R provides at least an oral biofilm anti-attachment benefit, as discussed above, and may be independently selected from:

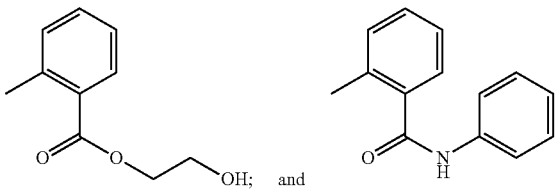

In some embodiments, R provides an oral biofilm anti-attachment benefit by interacting with oral bacteria to disable it from attaching to an oral surface. In some embodiments, R interacts with adhesins, ligands, or other moieties on the surface of oral bacteria that would ordinarily facilitate a linkage with a receptor or other moiety on the oral surface. In some embodiments, R provides an oral biofilm anti-attachment benefit by interacting with an oral surface to form a protective layer, such that the bacteria and biofilm components cannot adhere to the oral or tooth surface, thereby preventing an initial anchoring layer from forming on the oral surface. In some embodiments, R may substantially cover an oral surface, and prevent attachment of the bacteria and other components of the biofilm matrix.

In some embodiments, R provides at least an anti-oxidant benefit, as discussed above, and may be independently selected from:

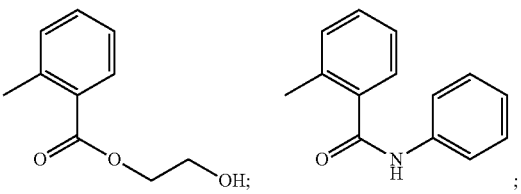

-continued

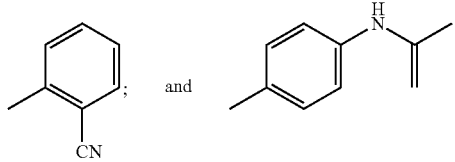

In some embodiments, R provides an anti-oxidant benefit by terminating a free radical chain reaction. In some embodiments, R removes free radical intermediates. In some embodiments, R inhibits other oxidation reactions by being oxidized itself without generating a free radical. In some embodiments, R provides an anti-oxidant benefit efficacy comparable to existing anti-oxidants. In some embodiments, R provides an anti-oxidant benefit efficacy comparable to Vitamin E.

In some embodiments, R provides at least an anti-inflammatory benefit and may be independently selected from:

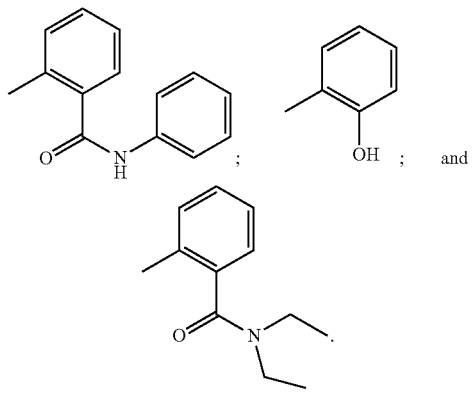

In some embodiments, R provides an anti-inflammation benefit by inhibiting the production and/or release of at least one chemical agent involved in inflammation. In some embodiments, R inhibits the production and/or release of GM-CSF. In some embodiments, R inhibits the production and/or release of IL-1b. In some embodiments, R inhibits the production and/or release of IL-6. In some embodiments, R inhibits the production and/or release of IL-8. In some embodiments, R inhibits the production and/or release of TNF-α. In some embodiments, R provides an anti-inflammation benefit efficacy comparable to existing anti-inflammatory agents. In some embodiments, R provides an anti-inflammation benefit efficacy comparable to triclosan.

In some embodiments, R provides at least an anti-microbial benefit and may be independently selected from:

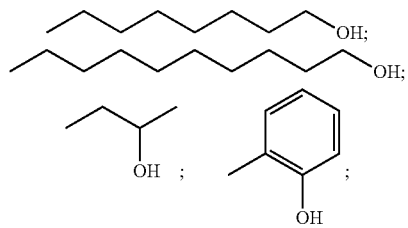

-continued

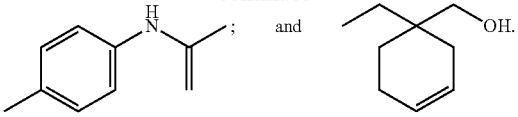

In some embodiments, R provides an anti-microbial benefit by perturbing the lipid fraction of microrganism plasma membrane. In some embodiments, R alters microbial membrane permeability resulting in leakage of intracellular materials and cell death. In some embodiments, R crosses microbial cell membranes, penetrating into the interior of the cell and interacting with intracellular sites critical for antimicrobial activity.

In some embodiments, a composition in accordance with the present invention comprises at least one menthol-derivative compound of Formula 1, wherein at least one compound is:

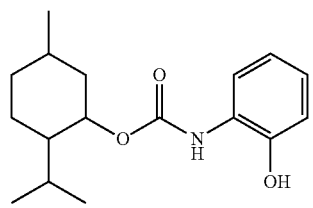

2isopropyl-5-methylcyclohexyl 2-hydroxyphenylcarbamate.

In some embodiments, a composition in accordance with the present invention comprises at least one menthol-derivative compound of Formula 1, wherein at least one compound is:

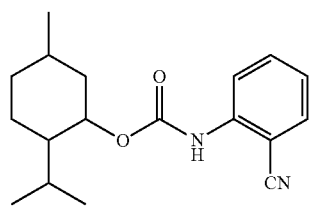

2isopropyl-5-methylcyclohexyl 2-cyanophenylcarbamate.

In some embodiments, a composition in accordance with the present invention comprises at least one menthol-derivative compound of Formula 1, wherein at least one compound is:

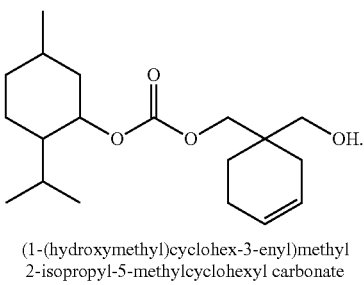 [SMILES: CC1CCC(C(C)C)C(OC(=O)OCC2(CO)CC=CCC2)C1]

(1-(hydroxymethyl)cyclohex-3-enyl)methyl 2-isopropyl-5-methylcyclohexyl carbonate In some embodiments, a composition in accordance with the present invention comprises at least one menthol-derivative compound of Formula 1, wherein at least one compound is:

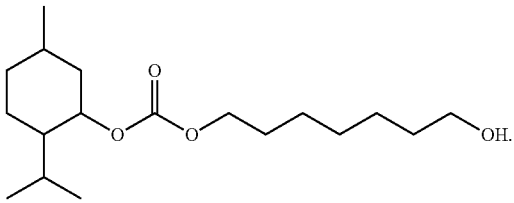

7-hydroxyheptyl 2-isopropyl-5-methylcyclohexyl carbonate

In some embodiments, a composition in accordance with the present invention comprises at least one menthol-derivative compound of Formula 1, wherein at least one compound is:

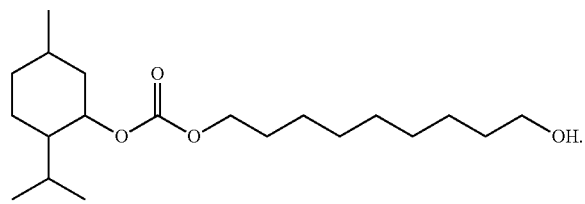

9-hydroxynonyl 2-isopropyl-5-methylcyclohexyl carbonate

In some embodiments, a composition in accordance with the present invention comprises at least one menthol-derivative compound of Formula 1, wherein at least one compound is:

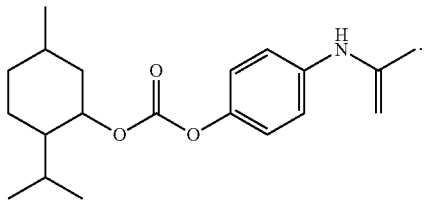

2-isopropyl-5-methylcyclohexyl 4-(prop-1-en-2-ylamino)phenyl carbonate

In some embodiments, a composition in accordance with the present invention comprises at least one menthol-derivative compound of Formula 1, wherein at least one compound is:

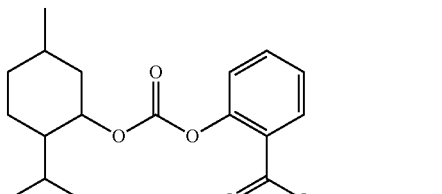

2-hydroxyethyl 2-((2-isopropyl-5-methylcyclohexyloxy)carbonyloxy)benzoate

In some embodiments, a composition in accordance with the present invention comprises at least one menthol-derivative compound of Formula 1, wherein at least one compound is:

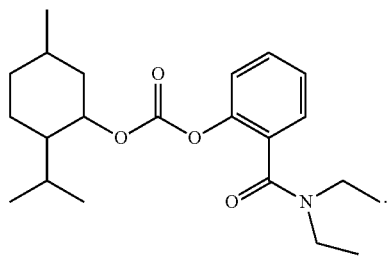

2-(diethylcarbamoyl)phenyl 2-isopropyl-5-methylcyclohexyl carbonate

In some embodiments, a composition in accordance with the present invention comprises at least one menthol-derivative compound of Formula 1, wherein at least one compound is:

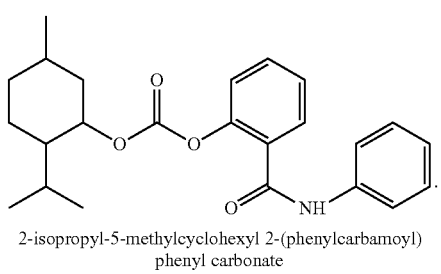 [SMILES: CC1CCC(C(C)C)C(OC(=O)Oc2ccccc2C(=O)Nc2ccccc2)C1]

2-isopropyl-5-methylcyclohexyl 2-(phenylcarbamoyl) phenyl carbonate

In some embodiments, a composition in accordance with the present invention comprises at least one menthol-derivative compound of Formula 1, wherein at least one compound is:

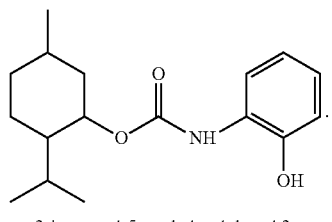

2-isopropyl-5-methylcyclohexyl 2-hydroxyphenylcarbamate

In some embodiments, a composition in accordance with the present invention comprises at least one menthol-derivative compound of Formula 1, wherein at least one compound is:

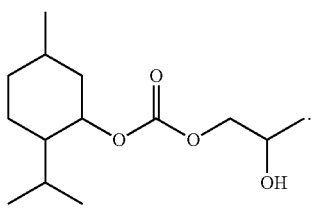

2-hydroxypropyl 2-isopropyl-5-methylcyclohexyl carbonate

B. Excipients

In some embodiments, a composition in accordance with the present invention includes at least one excipient. Excipients suitable for use in the present invention include any compound that is conventionally used in oral and/or topical compositions and that does not alter the efficacy of a menthol-derivative compound of Formula 1.

1. Oral Compositions

Suitable excipients for an oral composition in accordance with the present invention include, but are not limited to: preservatives, abrasives (smoothing agents), further antibacterial agents, inflammation-inhibiting agents, irritation-preventing agents, irritation-inhibiting agents, further antimicrobial agents, antioxidants, binders, (mineral) fillers, buffers, carrier materials, chelating agents (chelate formers), cleaning agents, care agents, surface-active substances, emulsifiers, enzymes, foam-forming agents, foam stabilizers, foam boosters, gelling agents, gel-forming agents, bleaching agents, smell- and/or taste-modulating agents, smell- and/or taste-reducing agents, smell- and/or taste-enhancing agents, plasticizers, (mucous membrane)/skin cooling agents (cooling substances), (mucous membrane)/skin soothing agents (mucous membrane)/skin cleansing agents, (mucous membrane)/skin care agents, (mucous membrane)/skin healing agents, mucous membrane-protecting agents, stabilisers, suspending agents, vitamins, colorants, colour-protecting agents, pigments, surfactants, electrolytes, silicone derivatives, polyols, calcium carbonate, calcium hydrogen phosphate, aluminium oxide, fluorides, zinc, tin, potassium, sodium and strontium salts, pyrophosphates, hydroxyapatites.

a. Flavouring Agents

In some embodiments, an oral composition in accordance with the present invention includes a flavouring agent. In some embodiments, the flavouring agent is a member chosen from: mucous membrane cooling agents, mucous membrane warming agents, sharp-tasting substances, sweeteners, sugar substitutes, organic or inorganic acidifiers (e.g., malic acid, acetic acid, citric acid, tartaric acid, phosphoric acid), bitter principles (e.g., quinine, caffeine, limonine, amarogentine, humolones, lupolones, catechols, tannins), edible mineral salts (e.g., sodium chloride, potassium chloride, magnesium chloride and sodium phosphates), essential oils (e.g., oils of spearmint, peppermint, wintergreen, sassafras, clove, sage, eucalyptus, marjoram, cinnamon, lemon, lime, grapefruit, and orange), menthol, carvone, anethole, and combinations thereof.

b. Abrasives

Abrasives suitable for use in the present invention include silica materials and particularly silica gels and precipitated amorphous silica having an oil absorption value of less than 100 cc/100 g silica and preferably in the range of from 45 cc/100 g to less than 70 cc/100 g silica. Oil absorption values are measured using the ASTM Rub-Out Method D281. Low oil absorption silica abrasives particularly useful in the practice of the present invention are marketed under the trade designation Sylodent® XWA (Davison Chemical Division of W. R. Grace & Co., Baltimore, Md. 21203). Sylodent® 650 XWA, a silica hydrogel composed of particles of colloidal silica having a water content of 29% by weight averaging from 7 to 10 microns in diameter, and an oil absorption of less than 70 cc/100 g of silica is a preferred example of a low oil absorption silica abrasive useful in the practice of the present invention. Another low oil absorption silica abrasive particularly useful in the practice of the present invention is marketed under the trade designation DP-105™ (J. M. Huber Chemicals Division, Havre de Grace, Md. 21078) is a precipitated amorphous silica having an average particle size distribution from 5 to 12 microns and an oil absorption in the range of 50 to 70 cc/100 g. Other abrasives which may be used in the practice of the present invention include precipitated silicas having a mean particle size of up to 20 microns, such as Zeodent® 115, (J. M. Huber Chemicals Division, Havre de Grace, Md. 21078), or Sylodent® 783 (Davison Chemical Division of W. R. Grace & Company), sodium metaphosphate, potassium metaphosphate, tricalcium phosphate, dihydrated dicalcium phosphate, aluminum silicate, calcined alumina, bentonite or other siliceous materials, or combinations thereof.

In some embodiments, an oral composition in accordance with the present invention includes an abrasive excipient. In some embodiments, the abrasive excipient is a silica material. In some embodiments, the silica material is colloidal particles having an average particle size ranging from 3 microns to 12 microns. In some embodiments, the colloidal particles have an average particle size ranging from 5 to 10 microns and a pH range from 4 to 10 preferably 6 to 9 when measured as a 5 wt. % slurry. In some embodiments, the silica material is a low oil absorption silica abrasive. In some embodiments, the low oil absorption silica abrasive is present in the oral care compositions of the present invention at a concentration of 5 wt. % to 40 wt. %. In some embodiments, the low oil absorption silica abrasive is present at a concentration of 10 wt. % to 30 wt. %.

In some embodiments, the abrasive excipient is a member chosen from: silicic acids, calcium carbonates, calcium phosphates, aluminium oxides and/or hydroxyapatites, sodium metaphosphate, potassium metaphosphate, tricalcium phosphate, dihydrated dicalcium phosphate, aluminum silicate, calcined alumina, bentonite, surface-active substances (e.g., sodium lauryl sulfate, sodium lauryl sarcosinate, and cocamidopropylbetaine), and other siliceous materials, and combinations thereof.

In some embodiments, the abrasive excipient may be used individually as the sole abrasive in preparing an oral composition of the present invention or in combination with other known dentifrice abrasives. In some embodiments, the total quantity of abrasive excipient present in the dentifrice compositions of the present invention is 5 wt. % to 60 wt. %. In some embodiments, the abrasive excipient is present in an amount of 10 wt. % to 55 wt. % by weight when the dentifrice composition is a toothpaste.

c. Anti-Microbial Agents

Anti-microbial agents suitable for use in the present invention include nonionic antibacterial agents, including halogenated diphenyl ether compounds such as 2,4,4-trichloro-2'-hydroxydiphenyl ether (Triclosan) and 2,2'-dihydroxy-5,5'-dibromodiphenyl ether. Other useful nonionic antibacterial agents include phenolic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference.

In some embodiments, an oral composition in accordance with the present invention includes an anti-microbial agent. In some embodiments, the anti-microbial agent is a member chosen from triclosan, chlorhexidine and its salts (e.g., its acetate, gluconate or hydrochloride), peroxides, phenols and their salts, domiphen bromide (phenododecinium bromide), bromochlorophene, Zn salts, chlorophylls, Cu salts, Cu gluconate, Cu chlorophyll, sodium lauryl, sulfate, quarternary monoammonium salts such as cocoaliphaticbenzyldimethylammonium chloride or also pyridinium salts such as cetyl pyridinium chloride, and combinations thereof.

In some embodiment, the anti-microbial agent is a nonionic antibacterial agent. In some embodiments, the nonionic antibacterial agent is included in a dentifrice composition at a concentration of 0.10 wt. % to 5 wt. %. In some embodiments, the nonionic antibacterial agent is present in an amount of 0.3 wt. % to 1.2 wt. %.

d. Anti-Caries Agents

In some embodiments, an oral composition in accordance with the present invention includes an anti-caries agent. In some embodiments, the anti-caries agent is a fluoride ion source chosen from: inorganic fluoride salts, such as soluble alkali metal, alkaline earth metal salts (e.g., sodium fluoride, potassium fluoride, ammonium fluoride, calcium fluoride), a copper fluoride such as cuprous fluoride, zinc fluoride, barium fluoride, sodium fluorosilicate, ammonium fluorosilicate, sodium fluorozirconate, ammonium fluorozirconate, sodium monofluorphosphate, aluminum mono- and di-fluorophosphate, fluorinated sodium calcium pyrophosphate, and combinations thereof.

e. Dentifrice Vehicles

In some embodiments, an oral composition in accordance with the present invention includes an orally acceptable dentifrice vehicle. In some embodiments, the dentifrice vehicle includes a humectant therein. Humectants suitable for use in the present invention include glycerin, sorbitol, xylitol, and/or propylene glycol of molecular weight in the range of 200 to 1,000. As used herein, "sorbitol" refers to the material typically commercially available as a 70% aqueous solution. In some embodiments, the humectant concentration is from 5 wt. % to 70 wt. % of the oral composition.

In some embodiments, an oral composition in accordance with the present invention includes water. Water employed in the preparation of commercially suitable toothpastes should preferably be deionized and free of organic impurities. In some embodiments, water is present in an amount of 15 wt. % to 30 wt. % of the oral composition. In some embodiments, water is present in an amount of 10 wt. %. In some embodiments, these amounts of water include the free water which is added in addition to that which is introduced with other materials such as with sorbitol.

f. Surfactants

Surfactants suitable for use in the compositions of the present invention include any material able to achieve increased prophylactic action and render the compositions more cosmetically acceptable. The surfactant is preferably a detersive material that imparts to the composition detersive and foaming properties.

In some embodiments, an oral composition in accordance with the present invention includes a surfactant. In some embodiments, an oral composition in accordance with the present invention includes a combination of surfactants. In some embodiments, the surfactant is an anionic surfactant including higher alkyl sulfates such as sodium lauryl sulfate. In some embodiments, the surfactant is an enzyme-compatible surfactants chosen from: nonanionic polyoxyethylene surfactants such as Pluronic® F127, Polyoxamer 407, Steareth 30, Polysorbate 20; and amphoteric surfactants such as cocamidopropyl betaine and cocamidopropyl betaine lauryl glucoside. In some embodiments, an oral composition in accordance with the present invention includes a surfactant or a combination of surfactants at a total surfactant concentration in the dentifrice composition of 2 wt. % to 10 wt. %. In some embodiments, the surfactant or combination of surfactants is present in an amount of 3.5 wt. % to 6.5 wt % by weight.

g. Anti-Tartar Agents

In some embodiments, an oral composition in accordance with the present invention includes an anti-tartar agent. In some embodiments, the anti-tartar agent is chosen from: pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate; long chain polyphosphates such as sodium hexametaphosphate; and cyclic phosphates such as sodium trimetaphosphate. In some embodiments, an anti-tartar agent is present in a dentifrice composition of the present invention at a concentration of 1 wt. % to 5 wt. %.

h. Thickening Agents

In some embodiments, an oral composition in accordance with the present invention includes a thickening agent. In some embodiments, the thickening agent is an organic thickener chosen from natural and synthetic gums and colloids including cellulose thickeners such as carboxymethyl cellulose; hyroxyalkyl celluloses such as hydroxypropyl cellulose hydroxyethyl cellulose; gums such as xanthan gum; polyglycols of varying molecular weights sold under the tradename Polyox™; and polyethylene glycol. In some embodiments, the thickening agent is an inorganic thickener chosen from: amorphous silica compounds such as colloidal silicas compounds available under the trade designation Cab-o-Sil® (manufactured by Cabot Corporation and distributed by Lenape Chemical, Bound Brook, N.J.); Zeodent® 165 (J.M. Huber Chemicals Division, Havre de Grace, Md. 21078); Sylodent® (Davison Chemical Division of W.R. Grace Corporation, Baltimore, Md. 21203); natural and synthetic clays; lithium magnesium silicate (Laponite); and magnesium aluminum silicate (Veegum). In some embodiments, the thickening agent is present in a dentifrice composition of the present invention in amounts of 0.1 wt. % to 10 wt. %. In some embodiments, the thickening agent is present in an amount of 0.5 wt. % to 4.0 wt. %.

i. Anti-Oxidants

In some embodiments, a composition in accordance with the present invention includes an anti-oxidant. In some embodiments, the anti-oxidant is chosen from: naturally occurring tocopherols and their derivatives (e.g., Vitamin E acetate), Vitamin C and its salts and derivatives (e.g., ascorbyl palmitate, Mg ascorbyl phosphate, ascorbyl acetate), Vitamin A and derivatives (Vitamin A palmitate), tocotrienols, flavonoids, alpha-hydroxy acids (e.g., citric acid, lactic acid, malic acid, tartaric acid) and their Na, Ka and Ca salts, flavonoids, quercetin, phenolic benzylamines, propyl gallate, octyl gallate, dodecyl gallate, butylhydroxyanisole (BHA, E320), butylhydroxytoluene (BHT, 2,6-di-tert.-butyl-4-methylphenol, E321), lecithins, mono- and diglycerides of edible fatty acids esterified with citric acid, carotenoids, carotenes (e.g., α-carotene, β-carotene, lycopene) and their derivatives, phytic acid, lactoferrin, EDTA, EGTA), folic acid and its derivatives, ubiquinone and ubiquinol and their derivatives, ferulic acid and its derivatives, zinc and its derivatives (e.g., ZnO, $ZnSO_4$), selenium and its derivatives (e.g., selenium methionine), orthophosphates and Na, K and Ca salts of mono-phosphoric acids, and constituents, extracts and fractions thereof isolated from plants, (e.g., tea, green tea, algae, grapeseeds, wheat germ, camomile, rosemary, oregano), and combinations thereof.

2. Topical Compositions

Suitable excipients for a topical composition in accordance with the present invention include, but are not limited to: solvents, preservatives, abrasives (smoothing agents), further antibacterial agents, inflammation-inhibiting agents, irritation-preventing agents, irritation-inhibiting agents, further antimicrobial agents, antioxidants, astringents, antistatics, binders, (mineral) fillers, buffers, carrier materials, chelating agents (chelate formers), cleaning agents, care agents, surface-active substances, deodorizing agents, emulsifiers, enzymes, fibres, film-forming agents (film-forming substances), fixatives, foam-forming agents, substances for preventing foaming, foam stabilizers, foam boosters, gelling agents, gel-forming agents, moisture-preserving agents (moisturizers), humectants, moisture-retaining substances, bleaching agents, brighteners (e.g., hydrogen peroxide), impregnating agents, friction-reducing agents, lubricants, smell- and/or taste-modulating agents smell- and/or taste-reducing agents, smell- and/or taste-enhancing agents, opacifiers, plasticizers, covering agents, lightening agents, silicones, (mucous membrane)/skin cooling agents (cooling substances), (mucous membrane)/skin soothing agents (mucous membrane)/skin cleansing agents, (mucous membrane)/skin care agents, (mucous membrane)/skin healing agents, mucous membrane-protecting agents, UV filters, stabilisers, suspending agents, vitamins, fatty oils, waxes, greases, phospholipids, saturated fatty acids, singly or multiply unsaturated fatty acids, alpha-hydroxy acids, polyhydroxy acids, liquifiers, colorants, colour-protecting agents, pigments, surfactants, electrolytes, silicone derivatives, polyols, organic solvents, silicic acids, calcium carbonate, calcium hydrogen phosphate, aluminium oxide, fluorides, zinc, tin, potassium, sodium and strontium salts, pyrophosphates, hydroxyapatites.

a. Solvents

In some embodiments, a topical composition in accordance with the present invention includes a solvent. In some embodiments, the solvent is selected from the radical consisting of, but not limited to: water or aqueous solutions; oils such as triglycerides of capric or capryl acid; and alcohols, diols or polyols and their ethers, preferably ethanol, isopropanol, propylene glycol, glycerol, ethylene glycol, and combinations thereof.

b. Thickeners

In some embodiments, a composition in accordance with the present invention includes a thickener. In some embodiments, the thickener is chosen from: calcium carbonate, titanium dioxide, silicon dioxide, talcum, aluminium oxide, dicalcium phosphate, tricalcium phosphate, magnesium hydroxide, cellulose thickeners such as carboxymethyl cellulose, hyroxyaliphatic celluloses such as hydroxypropyl cellulose hydroxyethyl cellulose, gums such as xanthan gum, polyglycols and polyethylene glycol, inorganic thickeners (e.g., amorphous silica compounds, natural and synthetic clays, lithium magnesium silicate and magnesium aluminum silicate), and combinations thereof.

EXAMPLES

Example 1

The bacterial anti-attachment activity of a selected radical of menthol carbonate/carbamate derivatives of the present invention was investigated using the crystal violate assay (SOP No. ATO-5345-00) in a 384-well plate over a 0.0004-2500 ppm concentration range. The anti-oxidant activity of the menthol carbonate/carbamate derivatives of the present invention was determined using the lipid peroxides assay (Kamiaya Biomedical Co., Seattle, Wash.) which is a colorimetric method that measures reduction of cumene hydroperoxide radicals. The anti-microbial test was performed according to the SOP No. ATO-5308-00 for determination of Minimal Inhibitory Concentration (MIC). The anti-inflammatory test was carried out according to SOP No. ATO-5307-00 measuring the percent inhibition of $PGE_2$. The results of these tests are summarized below in Table 1.

TABLE 1

Commonality in anti-attachment, anti-oxidant, anti-inflammatory, and anti-microbial activity for the specified menthol-derivative compounds.

| Anti-attachment | Anti-oxidant | Anti-inflammatory | Anti-microbial |
|---|---|---|---|
| | | | 2-hydroxypropyl 2-isopropyl-5-methylcyclohexyl carbonate |
| 2-isopropyl-5-methylcyclohexyl 2-(phenylcarbamoyl)phenyl carbonate | | | |

TABLE 1-continued

Commonality in anti-attachment, anti-oxidant, anti-inflammatory,
and anti-microbial activity for the specified menthol-derivative compounds.

| Anti-attachment | Anti-oxidant | Anti-inflammatory | Anti-microbial |
|---|---|---|---|
| | | 2-isopropyl-5-methylcyclohexyl 2-hydroxyphenylcarbamate | |
| | 2-isopropyl-5-methylcyclohexyl 2-cyanophenylcarbamate | | |
| | | 2-(diethylcarbamoyl)phenyl 2-isopropyl-5-methylcyclohexyl carbonate | |
| 2-isopropyl-5-methylcyclohexyl 4-(prop-1-en-2-ylamino)phenyl carbonate | | | 2-isopropyl-5-methylcyclohexyl 4-(prop-1-en-2-ylamino)phenyl carbonate |
| 2-hydroxyethyl 2-((2-isopropyl-5-methylcyclohexyloxy)carbonyloxy)benzoate | | | |
| | | | (1-(hydroxymethyl)cyclohex-3-enyl)methyl 2-isopropyl-5-methylcyclohexyl carbonate |

TABLE 1-continued

Commonality in anti-attachment, anti-oxidant, anti-inflammatory, and anti-microbial activity for the specified menthol-derivative compounds.

| Anti-attachment | Anti-oxidant | Anti-inflammatory | Anti-microbial |
|---|---|---|---|
| | | | 7-hydroxyheptyl 2-isopropyl-5-methylcyclohexyl carbonate |
| | | | 9-hydroxynonyl 2-isopropyl-5-methylcyclohexyl carbonate |

Example 2

5000 ppm of 2-isopropyl-5-methylcyclohexyl 2-hydroxyphenyl carbamate was formulated into toothpaste. One percent of cool crisp mint extra flavor was used to dissolve the menthol-derivative compound. A placebo was formulated without the menthol-derivative compound. The dentifrice composition is summarized below in Table 2.

TABLE 2

Dentifrice Composition Including 2-isopropyl-5-methylcyclohexyl 2-hydroxyphenyl carbamate.

| Step | M/X # | Ingredients | Weight % | Theoretical Weight |
|---|---|---|---|---|
| 1 | 660804 | CP purified water | 22.000 | 110.0000 |
| | 06076 | sodium saccharin USP | 0.3000 | 1.5000 |
| | 06448 | sodium fluoride USP | 0.2430 | 1.2150 |
| 2 | 06419 | 99.0%-101.0% synthetic glycerin | 20.000 | 100.0000 |
| | 06198 | titanium dioxide USP, FCC | 0.5000 | 2.5000 |
| | 12091 | sorbitol—non/browning, non-crystallizing | 20.8500 | 104.2500 |
| 3 | 06208 | propylene glycol USP | 0.5000 | 2.5000 |
| | 12212 | sodium CMC 2000S-12 USP | 1.100 | 5.5000 |
| | 00527 | IOTA carrageenan (LB9505) | 0.4000 | 2.000 |
| 4 | 06993 | dental silica (Zeodent ® 115) abrasive | 20.0000 | 100.0000 |
| | 01885 | dental silica thickener (Zeodent ® 165) | 1.5000 | 7.5000 |
| 5 | 890259 | cool crisp mint extra flavor (K91-4448) | 1.0000 | 5.0000 |
| | | 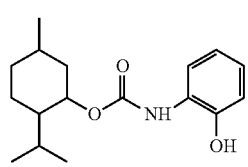 2-isopropyl-5-methylcyclohexyl 2-hydroxyphenylcarbamate | 0.5000 | 2.5000 |
| | 06286 | sodium lauryl sulfate powder NF | 1.5000 | 7.5000 |
| | | TOTAL Weight %/batch size | 100.0000 | 500.0000 |

A. Uptake and Aging

The dentifrice composition of Example 2 was evaluated for its uptake on HAP disk. Results shown below in Table 3 indicated that the uptake of the menthol-derivative compound, 2-isopropyl-5-methylcyclohexyl 2-hydroxyphenyl carbamate (0.5% in formula), is much lower than that of triclosan (0.3% in Colgate Total®). However, a mixed Example 2 and Total® slurry resulted in increase uptake of menthol-derivative compound. This observation suggests that the Gantrez® polymer which was lacking in Example 2 but in Total® may improve the uptake of 2-isopropyl-5-methylcyclohexyl 2-hydroxyphenyl carbamate. Gantrez® is a water-swellable synthetic, anionic, linear copolymeric polycarboxylate used for optimizing anticalculus effectiveness of linear compounds in dentifrice compositions. Recovery of the menthol-derivative compound from a 3-month old composition at room temperature detected with HPLC is 100%.

TABLE 3

Uptake of 2-isopropyl-5-methylcyclohexyl 2-hydroxyphenyl carbamate.

| Sample | ppm |
|---|---|
| 0.5% 2-isopropyl-5-methylcyclohexyl 2-hydroxyphenyl carbamate | 15 |
| 0.25% 2-isopropyl-5-methylcyclohexyl 2-hydroxyphenyl carbamate + 0.25% Gantrez ® polymer | 17 |

B. Anti-Inflammation

The anti-inflammatory activity of 2-isopropyl-5-methylcyclohexyl 2-hydroxyphenyl carbamate was tested in $PGE_2$ assay and compared to Triclosan. The anti-inflammatory activity of the menthol-derivative compound of the present invention is comparable to Triclosan based on this assay (Table 4).

TABLE 4

Efficacy of Pure Compounds in $PGE_2$ Assay.

| Pure Compound | $IC_{50}$ |
|---|---|
| 2-isopropyl-5-methylcyclohexyl 2-hydroxyphenyl carbamate | 0.38 μM |
| Triclosan | 0.48 μM |

The menthol-derivative compound of the present invention was further evaluated in 5-plex assay by using luminex. Results shown in Table 5 demonstrate that 2-isopropyl-5-methylcyclohexyl 2-hydroxyphenyl carbamate significantly inhibits IL-6 and TNF-α production.

TABLE 5

Efficacy of Pure Compounds in 5-plex Assay by Using Luminex (reduction of untreated control).

| Pure Compound | GM-CSF | IL-1b | IL-6 | TNF-α |
|---|---|---|---|---|
| 2-isopropyl-5-methylcyclohexyl 2-hydroxyphenyl carbamate | 6% | 13% | 33% | 81% |
| Triclosan | 4% | 13% | 37% | 58% |

The anti-inflammatory activity of a dentifrice composition including 2-isopropyl-5-methylcyclohexyl 2-hydroxyphenyl carbamate was tested in $PGE_2$ assay and compared with a matching placebo and Colgate Total®. The anti-inflammatory function of the dentifrice including 2-isopropyl-5-methylcyclohexyl 2-hydroxyphenyl carbamate was comparable to Total® and better than the matching placebo based on this assay (see FIG. 1). The dentifrice composition including 2-isopropyl-5-methylcyclohexyl 2-hydroxyphenyl carbamate also demonstrated its effeicacy on other cytokines (Table 6).

TABLE 6

Efficacy of Dentifrice Composition Including 2-isopropyl-5-methylcyclohexyl 2-hydroxyphenyl carbamate in 5-plex assay by Using Luminex (reduction of untreated control).

| Pure Compound | GM-CSF | IL-1b | IL-6 | IL-8 | TNF-α |
|---|---|---|---|---|---|
| Dentifrice Composition including: 2-isopropyl-5-methylcyclohexyl 2-hydroxyphenyl carbamate | 76% | 6% | 97% | 21% | 99% |
| Placebo | 46% | 0% | 67% | 0% | 91% |
| Colgate Total ® | 37% | 37% | 93% | — | 96% |
| CDC | 12% | 9% | 83% | — | 83% |

C. Anti-Oxidant

The menthol-derivative compound 2-isopropyl-5-methylcyclohexyl 2-hydroxyphenyl carbamate showed comparable anti-oxidant efficacy with Vitamin E in simple solution (see FIG. 2). A dentifrice composition including 2-isopropyl-5-methylcyclohexyl 2-hydroxyphenyl carbamate showed comparable efficacy compared to a matching placebo (see FIG. 3).

D. Anti-Bone Loss

The menthol-derivative compound 2-isopropyl-5-methylcyclohexyl 2-hydroxyphenyl carbamate significantly suppressed MMP-13 mRNA stimulated by parathyroid hormone (PTH) for 4 hours (see FIG. 4). This suggests that 2-isopropyl-5-methylcyclohexyl 2-hydroxyphenyl carbamate could potentially provide an anti-bone loss benefit.

E. Anti-Microbial

The menthol-derivative compound 2-isopropyl-5-methylcyclohexyl 2-hydroxyphenyl carbamate showed good anti-microbial efficacy by using the minimal inhibition concentration (MIC) test (Table 7).

TABLE 7

In Vitro Anti-Microbial Efficacy.

| Compound | MIC (against A.v) |
|---|---|
| 2-isopropyl-5-methylcyclohexyl 2-hydroxyphenyl carbamate | 4.9 ppm |
| Triclosan | 1.9 ppm |

The menthol-derivative compound 2-isopropyl-5 methylcyclohexyl 2-hydroxyphenyl carbamate also showed good anti-microbial efficacy in an artificial mouth model (see FIG. 5).

F. Metabolite Expression

The menthol-derivative compounds of the present invention formulated in a toothpaste may have the ability to up-regulate or down-regulate at least one member chosen from: a compound generated by amino acid metabolism; a compound generated in the urea cycle; a compound generated in glutathion conversion; a compound generated in lipid metabolism; a compound generated in carbohydrate metabolism; a compound generated by nucleic acid metabolism; vitamins; and co-factors.

As discussed in the specification and the examples above, contacting an oral cavity with 2-isopropyl-5-methylcyclohexyl 2-hydroxyphenyl carbamate formulated in a toothpaste may down-regulate the production of the following biomarkers: GM-CSF, IL-1b, IL-6, IL-8, TNF-α, and MMP-13; wherein the down-regulation of the biomarker correlates with a reduction in at least one symptom associated with periodontal disease.

Contacting an oral cavity with 2-isopropyl-5-methylcyclohexyl 2-hydroxyphenyl carbamate formulated in a toothpaste may down-regulate the production of one or more of the following metabolites: inosine, hypoxanthine, guanosine, guanine, leucine, isoleucine, lysine, methionine, phenylalanine, proline, serine, threonine, tryptophan, tyrosine, valine, phenylacetic acid, α-hydroxyioscaproic acid, 5-amino valeric acid, choline, glycerol-3-phosphate, and N-acetylneuraminic acid.

Contacting an oral cavity with 2-isopropyl-5-methylcyclohexyl 2-hydroxyphenyl carbamate formulated in a toothpaste may up-regulate the production of one or more of the following metabolites; uric acid, reduced glutathione, oxidized glutathion, ascorbic acid, and glutamine.

What is claimed:

1. A method for providing one or more oral care beneficial effects, selected from anti-inflammation and anti-bone loss effects, to a subject in need thereof, comprising administering to the oral cavity of the subject an amount from 0.05 wt. % to 5 wt. % of at least one menthol-derivative compound conforming to Formula 1 to a subject:

Formula 1

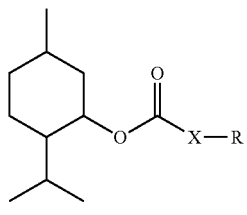

wherein

X is an oxygen atom or an NH radical; and

R is an unsubstituted or substituted aryl radical, and in combination with a water-swellable synthetic, anionic, linear copolymeric polycarboxylate.

2. The method of claim 1, wherein X is an NH radical.

3. The method of claim 2, wherein R is a substituted aryl radical.

4. The method of claim 3, wherein R is:

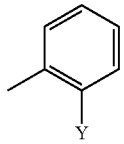

and wherein Y is a hydroxyl or cyano radical.

5. The method of claim 4, wherein the compound is:

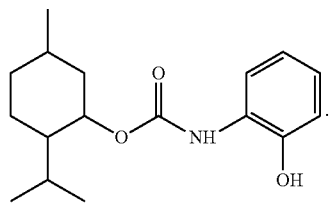 [SMILES: CC1CCC(C(C)C)C(OC(=O)Nc2ccccc2O)C1]

6. The method of claim 1, wherein X is an oxygen atom.

7. The method of claim 6, wherein R is at least one member chosen from:

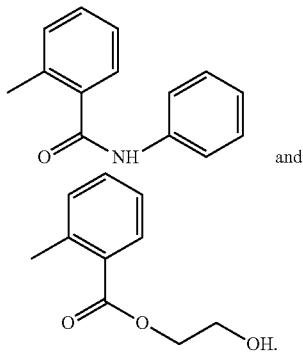

8. The method of claim 1, wherein the benefit is biofilm anti-attachment.

* * * * *